United States Patent [19]

Howes

[11] 4,438,011

[45] Mar. 20, 1984

[54] METHOD FOR STERILIZING SOFT CONTACT LENS

[75] Inventor: John G. B. Howes, Hertford Heath, England

[73] Assignee: Smith and Nephew Associated Companies Limited, England

[21] Appl. No.: 320,710

[22] Filed: Nov. 12, 1981

[30] Foreign Application Priority Data

Dec. 18, 1980 [GB] United Kingdom ............... 8040532

[51] Int. Cl.³ .......................... C11D 1/84; C11D 3/48
[52] U.S. Cl. ................................. 252/106; 252/174; 252/544; 134/42
[58] Field of Search ............... 252/106, 544, 541, 542, 252/174; 424/326; 134/42

[56] References Cited

U.S. PATENT DOCUMENTS

| | | | |
|---|---|---|---|
| Re. 29,693 | 7/1978 | Phares | 424/326 |
| 3,689,673 | 9/1972 | Phares | 424/326 |
| 3,843,782 | 10/1974 | Krezanoski et al. | 424/78 |
| 3,888,782 | 6/1975 | Boghosian et al. | 252/106 |
| 4,013,576 | 3/1977 | Loshaek | 252/106 |
| 4,285,738 | 8/1981 | Ogata | 134/26 |
| 4,354,952 | 10/1982 | Riedhammer et al. | 252/106 |

FOREIGN PATENT DOCUMENTS 46-26986 8/1971 Japan .
1432345 4/1976 United Kingdom .

Primary Examiner—P. E. Willis, Jr.
Attorney, Agent, or Firm—Jacobs & Jacobs

[57] ABSTRACT

A substantially isotonic, aqueous solution suitable for the sterilization of soft contact lenses having small or no propensity to cause ocular irritation which solution comprises a sterile aqueous solution of 0.00125 to 0.0025% of a chlorhexidine salt and sufficient tonicity adjusting agent to render the solution substantially isotonic said tonicity adjusting agent not containing ionic species producing a tonicity equivalent to more than a 0.3% solution of sodium chloride.

10 Claims, No Drawings

METHOD FOR STERILIZING SOFT CONTACT LENS

The present invention relates to sterilising solutions suitable for sterilising contact lenses and especially soft (hydrophilic) contact lenses and to the use of such solutions.

Soft contact lenses have proved difficult to sterilise in a manner that does not give rise to side effects. One of the most widely used sterilising methods for soft contact lenses is to soak the lenses for a period of hours in a dilute solution of a salt of chlorhexidine. U.S. Pat. No. RE. 29693 indicated that chlorhexidine could be used to sterilise soft contact lenses without causing irritation to the eye. Unfortunately when present at concentrations sufficient to sterilise lenses, chlorhexidine has been found to cause irritation in a considerable number of subjects. This irritation is believed to occur even at concentrations of chlorhexidine where its effectiveness has been thought by some to be doubtful. Although the aforementioned specification suggests that concentrations of chlorhexidine as low as 0.001% could be employed to sterilise soft contact lenses this has never been achieved in practice due to the insufficient effectiveness of such low concentrations of chlorhexidine especially against such organisms as *Candida albicans*. Clearly it would be desirable to find an effective sterilising solution which could utilise concentrations of chlorhexidine lower than those previously commercially employed. It has now been discovered that avoidance of high concentrations of ionic species can be used to enhance the effectiveness of solutions of chlorhexidine salts, for example the gluconate, containing from 0.00125 to 0.0025% so that effective sterilisation can occur at lower levels of chlorhexidine than have previously proved practicable without the use of additional antimicrobial agents being present.

It is particularly surprising that a solution of from 0.0015 to 0.002% of a chlorhexidine salt is so useful. Such solutions made isotonic with for example glycerol, propylene glycol or urea have shown in a microbiological "die-off" test, against important pathogens such as *Candida albicans*, an improved rate of kill against a similar solution made isotonic with sodium chloride. A similar test carried out in a lens case in the presence of a soft contact lens showed similar effective results. In use these solutions cause less ocular irritation than effective prior art solutions rendered isotonic with salt when the contact lens is replaced directly into the eye from the sterilising solution.

It is particularly surprising that solutions of from 0.00125 to 0.0025% of chlorhexidine gluconate or acetate have proved so useful even in the absence of thiomersal or the like and that solutions of from 0.0015 to 0.002% chlorhexidine gluconate can be used to such good effect.

The sterilising solutions of the present invention offer the advantages of effectiveness of lower levels of chlorhexidine than hve previously been practicable coupled with, in solutions suitable for sterilisation of contact lenses, the ability of replacing the lens in the eye without the need for re-equilibration or special washing techniques. Solutions containing the lower level of chlorhexidine are believed to reduce the propensity of the solution to cause ocular irritation.

It will be appreciated that when such low levels of chlorhexidine are employed it is particularly important that the solution has good storage properties since a lack of stability would soon deplete the chlorhexidine and render the sterilising solution less effective or even ineffective. It is one of the surprising advantages of this invention that solutions can be provided which have good storage stability.

A further advantage of this invention is that the sterilising solution is simple to prepare and does not involve any complicated procedures or extended list of mandatory ingredients as do recently invented solutions.

The present invention provides a substantially isotonic, aqueous solution suitable for the sterilisation of soft contact lenses having small or no propensity to cause ocular irritation which solution comprises 0.00125 to 0.0025% of a chlorhexidine salt and sufficient tonicity adjusting agent to render the solution substantially isotonic said tonicity adjusting agent containing ionic species producing a tonicity equivalent to not more than a 0.3% solution of sodium chloride.

Suitably the present invention provides a substantially isotonic aqueous soft lens sterilising solution which comprises 0.00125 to 0.0025% of a chlorhexidine salt and sufficient non-ionic tonicity adjusting agent to render the solution substantially isotonic.

Most suitably the solution of this invention is substantially free from ions since ionic species, for example chloride ions, depress the effectiveness of the solution. In general, apart from the chlorhexidine salt, the solution of this invention will not usually contain ionic materials producing a tonicity equivalent to more than a 0.25% solution of sodium chloride, more aptly not more than the equivalent of 0.2% sodium chloride and preferably not more than the equivalent of 0.15% sodium chloride, more preferably not more than the equivalent of 0.1% sodium chloride and most preferably no ionic materials. For the purpose of this specification ionic species mean those molecules which dissolve in water to yield separated ions but does not include those molecules which dissolve in water to yield electonically neutral molecules with separated charges (zwitter ions such as glycine).

From the foregoing it will be appreciated that in a preferred aspect the present invention comprises an effective concentration of a chlorhexidine salt characterised in that the solution is substantially free of other ions and especially free of chloride ions.

When used herein the term "substantially isotonic" means having a tonicity equivalent to a 0.7 to 1.2% solution of sodium chloride. The solutions of this invention will more aptly have a tonicity equivalent to a 0.8 to 1.0% and preferably 0.9% solution of sodium chloride.

Tonicity adjusting agents which may be employed are non-ionic materials such as polyhydric alcohols, for example propylene glycol, glycerol, glucose, lactose, mannitol and the like, glycine and urea. A preferred non-ionic isotonicity adjusting agent is propylene glycol. A further preferred non-ionic isotonicity adjusting agent is glycerol.

The preferred salt for use in the solutions of this invention is chlorhexidine gluconate (which is more aptly termed chlorhexidine digluconate although it is normally termed chlorhexidine gluconate). (The percentage chlorhexidine salt concentation is expressed in chlorhexidine gluconate equivalents).

The chlorhexidine salt will be present in the compositions of this invention by 0.00125 to 0.0025% and most suitably by 0.0015 to 0.002% for example 0.0015%, 0.0016%, 0.0017%, 0.00175%, 0.0018% or 0.002%.

From the foregoing it will be appreciated that in a preferred aspect this invention provides an aqueous isotonic soft lens sterilising solution which comprises a sterile aqueous solution of 0.0015 to 0.002% chlorhexidine gluconate rendered isotonic with a non-ionic tonicity adjusting agent.

The compositions of this invention may be prepared by dissolving the components in water. The resultant aqueous solution may be sterilised by filtration through a 0.22 micron cellulose ester membrane filter. The sterile solution may then be aseptically filled into pre-sterilised containers using conventional filling machinery. Alternatively the solution may be filled into a container which is capable of standing autoclaving temperatures, for example glass or polypropylene and the container and its contents sterilised after filling by autoclaving, for example at 116° C. for 30 minutes at 10 psi pressure.

Containers for compositions of this invention are made from materials which are sterilisable and will not absorb excessive amounts of the chlorhexidine ion from the composition. Suitable materials include low density polyethylene. Containers made from low density polyethylene may be sterilised using ethylene oxide or gamma irradiation and stored until required for filling. Such containers of polyethylene may be filled and stored without the composition unacceptably losing effectiveness through absorption of the chlorhexidine ion from the solution into the walls of the container. Suitable multi-dose containers will have a volume of 25 to 250 ml. Although it is preferred that the volume of the container is 100 to 150 ml, for example about 125 ml to contain solution for 20 to 30 days of daily use. Suitable multi-dose containers may be closed by a screw cap and the solution dispensed through a restricted opening such as a dropper tip. Alternatively, though not desirably, the compositions of the present invention may be filled into unit dose containers, for example sachets capable of containing 10 to 20 ml of solution.

In an important aspect, this invention provides a method of sterilising soft contact lenses which method comprises contacting said lens with a solution of this invention until sterilisation is affected.

Most suitably from 1 to 20 ml of solution of this invention is employed per lens to be sterilised and preferably from 3 to 12 ml, for example 5 or 10 ml of solution of this invention is employed per lens to be sterilised.

In general the lens is kept in contact with the solution of this invention from 3 to 10 hours, more suitably from 4 to 9 hours and usually from 6 to 8 hours. It is often convenient to sterilise the lens by maintaining it in a solution of this invention overnight.

In the method of the present invention the lens may be contacted with the aqueous solution in a lens case. Suitable lens cases will have a volume of between 1 and 20 ml and more suitably from 3 to 12 ml, for example 10 ml. The lens case may comprise a single chamber for receiving the solution. In such cases a lens holder capable of holding each lens from right and left eye separate from each other is required. Alternatively the lens case may comprise a pair of chambers (one for each lens). It is desirable that which ever type of lens case is used the lens is allowed to float freely in the solution so that the entire surface is wetted by the solution and thereby effectively sterilised. Suitable lens cases will be closed by a bacteria-proof closure so that bacteria are not admitted to the interior of the lens case during the sterilising cycle. The skilled worker will know the type of screw cap or snap top closure which is bacteria-proof.

Materials for use in manufacturing lens cases should not absorb the chlorhexidine ion from the solution during the sterilising cycle thereby adversely effecting the efficacy of the composition. Suitable materials include low density polyethylene.

The sterilising solutions of this invention can reduce bacterial contamination of the lenses more rapidly than analogous compositions which are rendered isotonic with sodium chloride. Thus a further aspect of this invention provides a method of enhancing the rate of kill of bacteria by chlorhexidine in a soft lens sterilising solution which method comprises including in the solution a concentration of non-ionic tonicity adjusting agent as hereinbefore indicated.

The solutions of this invention most preferably contain chlorhexidine as the only antimicrobial agent. However if desired small concentrations of other antibacterial agents such as thiomersal may be included, for example 0.00025 to 0.0025% thiomersal, more aptly 0.0003 to 0.001% thiomersal and more favourably 0.0004 to 0.0006% thiomersal, for example 0.0005% thiomersal. In general the concentration of chlorhexidine plus other antibacterial present in the solution of this invention should not exceed 0.0035%, more suitably should not exceed 0.003%, most suitably should not exceed 0.0025% and preferably should not exceed 0.002%. It is preferred not to employ antimicrobial agents other than chlorhexidine in this invention. It is one of the particularly surprising features of the invention that the solution is adequately preserved against fungi without the need to employ an additional agent.

The solutions of this invention may also be used for sterilising hard, silicone and the so-called gas permeable contact lenses. It is a considerable advantage to provide a solution which may be used to sterilise diverse types of contact lenses.

The following Examples illustrate the invention. The solutions may be prepared by mixing together the components in the specified concentrations.

EXAMPLE 1

| Sterilising Solution | |
|---|---|
| Chlorhexidine gluconate | 0.00125% |
| Glycerol | 2.5% |
| Distilled water | to 100% |

EXAMPLE 2

| Sterilising Solution | |
|---|---|
| Chlorhexidine gluconate | 0.0018% |
| Glycerol | 2.5% |
| Distilled water | to 100% |

EXAMPLE 3

| Sterilising Solution | |
|---|---|
| Chlorhexidine gluconate | 0.002% |
| Glycerol | 2.5% |
| Distilled water | to 100% |

EXAMPLE 4

| Sterilising Solution | |
|---|---|
| Chlorhexidine gluconate | 0.0015% |
| Thiomersal | 0.0005% |
| Glycerol | 2.5% |
| Distilled water | to 100% |

EXAMPLE 5

| Sterilising Solution | |
|---|---|
| Chlorhexidine gluconate | 0.0025% |
| Urea | 1.6% |
| Distilled water | to 100% |

EXAMPLE 6

| Sterilising Solution | |
|---|---|
| Chlorhexidine acetate | 0.002% |
| Glycerol | 2.5% |
| Distilled water | to 100% |

EXAMPLE 7

| Sterilising Solution | |
|---|---|
| Chlorhexidine gluconate | 0.0018% |
| Lactose | 9.75% |
| Distilled water | to 100% |

EXAMPLE 8

Sterilisation

A hydrophilic contact lens was placed into a closable lens case (volume 12 ml). A sterilising solution of Example 6 (10 ml) was introduced into the lens case which was then closed and left at ambient temperature for 6 hours. At the end of this time the lens was deemed to be satisfactorily sterilised.

Throughout this document % are given in a w/v basis. Concentrations of chlorhexidine salts are expressed as chlorhexidine gluconate equivalents (i.e. the concentration produced if the salt had the same molecular weight as chlorhexidine gluconate).

EXAMPLE 9

| Sterilising Solution | |
|---|---|
| Chlorhexidine gluconate | 0.00125% |
| Propylene glycol | 2.0% |
| Distilled water | to 100% |

EXAMPLE 10

| Sterilising Solution | |
|---|---|
| Chlorhexidine gluconate | 0.0015% |
| Propylene glycol | 2.0% |
| Distilled water | to 100% |

EXAMPLE 11

| Sterilising Solution | |
|---|---|
| Chlorhexidine gluconate | 0.002% |
| Propylene glycol | 2.0% |
| Distilled water | to 100% |

EXAMPLE 12

| Sterilising Solution | |
|---|---|
| Chlorhexidine gluconate | 0.002% |
| Glycine | 2.2% |
| Distilled water | to 100% |

EXAMPLE 13

| Sterilising Solution | |
|---|---|
| Chlorhexidine gluconate | 0.0018% |
| Propylene glycol | 2.0% |
| Distilled water | to 100% |

EXAMPLE 14

| Sterilising Solution | |
|---|---|
| Chlorhexidine gluconate | 0.002% |
| Propylene glycol | 1.78% |
| Sodium chloride | 0.1% |
| Distilled water | to 100% |

EXAMPLE 15

| Sterilising Solution | |
|---|---|
| Chlorhexidine gluconate | 0.0016% |
| Propylene glycol | 2.0% |
| Distilled water | to 100% |

Demonstration of Effectiveness 1

The microbiological effectiveness of 0.002% solutions of chlorhexidine gluconate made isotonic with sodium chloride, glycerol, glycine, propylene glycol and urea was investigated using the following test. Each test solution (20 ml) was dispensed into a sterile glass bottle. Each solution was then inoculated with 0.2 ml. of a $10^8$ organisms/ml suspension of the test organisms, *Staphylococcus aureus* NCTC 6571 and *Candida albicans* LSH 3153 to give a final concentration in the test solution of approximately $10^6$ organisms/ml. The inoculated bottles were held at ambient temperature, approximately 20° C. and at specified time intervals after inoculation $2 \times 1$ ml aliquots were removed. These aliquots were used in duplicate tests in which each aliquot was poured into a plate and a Triptone Soy Agar solution containing Tween 80 and lecithin to neutralise any chlorhexidine gluconate carried over was added. The plate were incubated at 37° C. for 24 hours and the number of colonies counted. The number of surviving organisms/ml at each time period was then calculated. The results are shown as follows:

|  | Staphyloccus aureus Survivors/ml after | | Candida albicans Survivors/ml |
| --- | --- | --- | --- |
|  | 2 hrs. | 4 hrs. | after 4 hrs. |
| 0.002% Chlorhexidine gluconate in | | | |
| Distilled water | <10 | <10 | <10 |
| 0.9% Sodium chloride | >$10^4$ | >$10^3$ | >$10^3$ |
| 1.63% Urea | <10 | <10 | <10 |
| 2.5% Glycerol | <10 | <10 | <10 |
| 2.2% Glycine | <10 | <10 | <10 |
| 2.0. Propylene glycol |  | <10 | <10 |
| 0.0016% Chlorhexidine gluconate in | | | |
| 2.0% Propylene glycol |  | <10 | <10 |

What we claim is:

1. A method of sterilizing a soft contact lens, which comprises contacting said lens for sufficient time to effect sterilization with a substantially isotonic, aqueous solution having small or no propensity to cause ocular irritation, said solution comprising a sterile aqueous solution of 0.00125 to 0.0025% of a chlorhexidine salt and sufficient nonionic tonicity adjusting agent to render the solution substantially isotonic, said tonicity adjusting agent containing ionic species producing a tonicity equivalent to not more than a 0.3% solution of sodium chloride.

2. A method according to claim 1, in which said aqueous solution contains from 0.0015 to 0.002% of said chlorhexidine salt.

3. A method according to claim 1, in which the tonicity adjusting agent contains ionic species producing a tonicity equivalent of not more than a 0.1% solution of sodium chloride.

4. A method according to claim 2, in which said aqueous solution is free from ionic species other than those arising from the chlorhexidine salt.

5. A method according to claim 4, in which the chlorhexidine salt is chlorhexidine gluconate.

6. A method according to claim 5, in which the tonicity adjusting agent is a polyhydric alcohol.

7. A method according to claim 5, in which the tonicity adjusting agent is glycerol.

8. A method according to claim 5, in which the tonicity adjusting is propylene glycol.

9. A method of sterilizing a soft contact lens, which comprises contacting said lens for a sufficient time to effect sterilization with a substantially isotonic, aqueous solution having small or no propensity to cause ocular irritation, said solution comprising a sterile aqueous solution of 0.00125 to 0.0025% of a chlorhexidine salt and an amout of an additional antibacterial agent such that the concentration of chlorhexidine salt and additional antibacterial agent does not exceed 0.0035% of the solution and sufficient nonionic tonicity adjusting agent to render the solution substantially isotonic, said tonicity adjusting agent containing ionic species producing a tonicity equivalent to not more than a 0.3% solution of sodium chloride.

10. A method according to claim 9, in which the solution contains from 0.00025 to 0.0025% of thiomersal as additional antibacterial agent.

* * * * *